United States Patent
Timm (10) Patent No.: US 7,699,875 B2
(45) Date of Patent: Apr. 20, 2010

(54) SPINAL STABILIZATION DEVICE WITH WELD CAP

(75) Inventor: Jens P. Timm, West Haven, CT (US)

(73) Assignee: Applied Spine Technologies, Inc., Rocky Hill, CT (US)

( * ) Notice: Subject to any disclaimer, the term of this patent is extended or adjusted under 35 U.S.C. 154(b) by 789 days.

(21) Appl. No.: 11/405,196

(22) Filed: Apr. 17, 2006

(65) Prior Publication Data
US 2007/0244481 A1    Oct. 18, 2007

(51) Int. Cl.
*A61B 17/70* (2006.01)
(52) U.S. Cl. .................. 606/254; 606/257; 606/259
(58) Field of Classification Search ............... 606/254, 606/255, 257, 259
See application file for complete search history.

(56) References Cited

U.S. PATENT DOCUMENTS

| | | | |
|---|---|---|---|
| 2,733,596 | A | 2/1956 | Painter |
| 4,328,960 | A | 5/1982 | Handke et al. |
| 4,352,514 | A | 10/1982 | Orima |
| 4,558,852 | A | 12/1985 | Steiner et al. |
| 4,650,167 | A | 3/1987 | Steiner et al. |
| 4,743,260 | A | 5/1988 | Burton |
| 4,759,769 | A | 7/1988 | Hedman et al. |
| 5,034,011 | A | 7/1991 | Howland |
| 5,071,264 | A * | 12/1991 | Franke et al. ............. 384/501 |
| 5,174,551 | A | 12/1992 | Mintgen |
| 5,180,393 | A | 1/1993 | Commarmond |
| 5,237,787 | A * | 8/1993 | Grether et al. ............ 52/171.3 |

(Continued)

FOREIGN PATENT DOCUMENTS

AU            744241            7/1999

(Continued)

OTHER PUBLICATIONS

Panjabi, The Stabilizing System of the Spine, Part I. Function, Dysfunction, Adaptation, and Enhancement, Journal of Spinal Disorders, 1992, vol. 5, No. 4, pp. 383-389.

(Continued)

*Primary Examiner*—Eduardo C Robert
*Assistant Examiner*—Julianna N Harvey
(74) *Attorney, Agent, or Firm*—McCarter & English, LLP (57) ABSTRACT

A weld cap is configured and dimensioned to interact with a resilient element, e.g., a spring, and a structural member, e.g., an end cap, so as to securely position the spring relative to the end cap. The weld cap functions to distance the welding process and associated welding energy from the spring, thereby avoiding and/or minimizing any potentially undesirable annealing effect associated with securing/welding the spring relative to the end cap. A first weld cap interacts with the spring at a first end region thereof, and a second weld cap interacts with the spring at a second end region thereof, thereby effectively securing the spring with respect to opposed end caps at either end of an elongated spinal stabilization device. Alignment grooves or channels may be provided for orienting or aligning the spring with respect to the end caps and weld caps. The end regions of the spring may also include bend regions that facilitate the assembly process and/or further minimize the freedom of movement of the spring relative to the end cap/weld cap combination. The dynamic stabilization device and associated system provide advantageous clinical results in spinal applications.

16 Claims, 8 Drawing Sheets

U.S. PATENT DOCUMENTS

| | | |
|---|---|---|
| 5,291,901 A | 3/1994 | Graf |
| 5,329,933 A | 7/1994 | Graf |
| 5,375,823 A | 12/1994 | Navas |
| 5,415,661 A | 5/1995 | Holmes |
| 5,423,816 A | 6/1995 | Lin |
| 5,480,401 A | 1/1996 | Navas |
| 5,501,684 A | 3/1996 | Schlapfer et al. |
| 5,505,118 A | 4/1996 | Arnesen et al. |
| 5,540,688 A | 7/1996 | Navas |
| 5,562,737 A | 10/1996 | Graf |
| 5,653,680 A | 8/1997 | Cruz |
| 5,672,175 A | 9/1997 | Martin |
| RE36,221 E | 6/1999 | Breard et al. |
| 5,961,516 A | 10/1999 | Graf |
| 6,162,223 A | 12/2000 | Orsak et al. |
| 6,176,860 B1 | 1/2001 | Howard |
| 6,241,730 B1 | 6/2001 | Alby |
| 6,267,764 B1 | 7/2001 | Elberg |
| 6,293,949 B1 | 9/2001 | Justis et al. |
| 6,375,681 B1 | 4/2002 | Truscott |
| 6,402,750 B1 | 6/2002 | Atkinson et al. |
| 6,419,706 B1 | 7/2002 | Graf |
| 6,440,169 B1 | 8/2002 | Elberg et al. |
| 6,508,818 B2 | 1/2003 | Steiner et al. |
| 6,554,831 B1 | 4/2003 | Rivard et al. |
| 6,645,207 B2 | 11/2003 | Dixon et al. |
| 6,761,719 B2 | 7/2004 | Justis et al. |
| 6,835,205 B2 | 12/2004 | Atkinson et al. |
| 2002/0095154 A1 | 7/2002 | Atkinson et al. |
| 2002/0151978 A1 | 10/2002 | Zacouto et al. |
| 2003/0055427 A1* | 3/2003 | Graf ..................... 606/61 |
| 2003/0171749 A1 | 9/2003 | Le Couedic et al. |
| 2003/0220642 A1 | 11/2003 | Freudiger |
| 2003/0220643 A1 | 11/2003 | Ferree |
| 2004/0049189 A1 | 3/2004 | Le Couedic et al. |
| 2004/0049190 A1 | 3/2004 | Biedermann et al. |
| 2004/0082954 A1 | 4/2004 | Teitelbaum et al. |
| 2004/0143264 A1 | 7/2004 | McAfee |
| 2004/0147928 A1 | 7/2004 | Landry et al. |
| 2004/0167523 A1 | 8/2004 | Jackson |
| 2005/0171543 A1* | 8/2005 | Timm et al. ............ 606/61 |
| 2006/0011243 A1* | 1/2006 | Jacobs et al. ........ 137/624.11 |
| 2006/0036240 A1 | 2/2006 | Colleran et al. ......... 606/61 |
| 2006/0264940 A1 | 11/2006 | Hartmann ............... 123/458 |
| 2007/0032123 A1* | 2/2007 | Timm et al. ............ 439/395 |

FOREIGN PATENT DOCUMENTS

| | | |
|---|---|---|
| CA | 2135838 | 5/1995 |
| CA | 2213058 | 2/1998 |
| EP | 0516567 | 12/1992 |
| EP | 0534874 | 3/1993 |
| EP | 0576379 | 12/1993 |
| EP | 0611554 | 8/1994 |
| EP | 0821917 | 2/1998 |
| EP | 1039855 | 6/2004 |
| FR | 2676911 | 12/1992 |
| FR | 2681520 | 3/1993 |
| FR | 2692468 | 12/1993 |
| FR | 2694182 | 2/1994 |
| FR | 2701650 | 8/1994 |
| FR | 2701651 | 8/1994 |
| FR | 2751864 | 2/1998 |
| FR | 2772594 | 6/1999 |
| FR | 2775891 | 9/1999 |
| FR | 2794362 | 12/2000 |
| FR | 2799949 | 4/2001 |
| FR | 2801782 | 6/2001 |
| FR | 2803188 | 7/2001 |
| FR | 2809304 | 11/2001 |
| FR | 2810873 | 1/2002 |
| FR | 2812535 | 2/2002 |
| GB | 2382304 | 5/2003 |
| JP | 6-285100 | 10/1994 |
| JP | 7-289562 | 11/1995 |
| JP | 10-71157 | 3/1998 |
| JP | 10-277070 | 10/1998 |
| WO | 99/32054 | 7/1999 |
| WO | 01/39678 | 6/2001 |
| WO | 01/45576 | 6/2001 |
| WO | 01/49192 | 7/2001 |
| WO | 02/00124 | 1/2002 |
| WO | 2002/102259 | 12/2002 |

OTHER PUBLICATIONS

Panjabi, The Stabilizing System of the Spine Part II. Neutral Zone and Instability Hypothesis, Journal of Spinal Disorders, 1992, vol. 5, No. 4, pp. 390-397.

* cited by examiner

SPINAL STABILIZATION DEVICE WITH WELD CAP

BACKGROUND

1. Technical Field

The present disclosure is directed to a spinal stabilization device/system that includes at least one spring member and at least one weld cap to facilitate secure interaction of the spring member with other structural components of the spinal stabilization device/system.

2. Background Art

Each year, over 200,000 patients undergo lumbar fusion surgery in the United States. While fusion is effective about seventy percent of the time, there are consequences even to these successful procedures, including a reduced range of motion and an increased load transfer to adjacent levels of the spine, which may accelerate degeneration at those levels. Further, a significant number of back-pain patients, estimated to exceed seven million in the U.S., simply endure chronic low-back pain, rather than risk procedures that may not be appropriate or effective in alleviating their symptoms.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, e.g., the Dynesys stabilization system (Zimmer, Inc.; Warsaw, Ind.) and the Graf Ligament. A major goal of this concept is the stabilization of the spine to prevent pain while preserving near normal spinal function.

To provide dynamic internal spinal stabilization, motion preservation devices may advantageously include dynamic junctions that exhibit multiple degrees of freedom and commonly include active force-absorbing/force-generating structures. Such structures may include one or more resilient elements, e.g., torsion springs and/or coil springs, designed and deployed so as to contribute strength and flexibility to the overall device. While the flexibility afforded by such resilient elements is plainly critical to the effectiveness of the respective devices of which they form a part, the elevated force levels associated with the use of such resilient elements can result in such resilient elements developing significant levels of internal stress. Depending on the magnitude and location thereof, internal stresses may pose the potential for stress-induced fatigue, material deformation and/or cracks. The FDA has promulgated rules (e.g., Title 21, Subchapter H, Part 888, Subpart D, Section 888.3070 regarding pedicle screw spinal systems) that, in relevant part, require manufacturers to demonstrate compliance with special controls, including but not limited to applicable mechanical testing standards geared toward high reliability and durability.

With the foregoing in mind, those skilled in the art will understand that a need exists for devices, systems and methods for motion-preserving spinal stabilization devices and systems having reliable, durable constructions. In addition, a need exists for manufacturing processes and/or techniques that may be used to reliably and efficiently produce motion-preserving spinal stabilization devices and systems. These and other needs are satisfied by the disclosed devices and systems that include advantageous spring junctions, as well as the associate methods for manufacture/assembly thereof.

SUMMARY OF THE DISCLOSURE

According to the present disclosure, advantageous devices, systems and methods for spinal stabilization are provided. According to exemplary embodiments of the present disclosure, the disclosed devices, systems and methods include a spring junction that promotes reliable and efficacious spinal stabilization. The disclosed spring junction includes a structural member that is mounted or mountable with respect to a spine attachment fastener, such as a pedicle screw, and a resilient element, e.g., a spring, affixed with respect to the structural member.

According to the present disclosure, a weld cap is configured and dimensioned to interact with the resilient element and the structural member so as to securely position the resilient element relative to the structural member. Moreover, the weld cap functions to advantageously distance the welding process and associated welding energy from the resilient element, thereby avoiding and/or minimizing any potentially undesirable annealing effect associated with securing/welding the resilient element relative to the structural member. According to exemplary embodiments of the present disclosure, a first weld cap interacts with the resilient element at a first end region thereof, and a second weld cap interacts with the resilient element at a second end region thereof, thereby effectively securing the resilient element with respect to opposed structural members at either end of an elongated spinal stabilization device.

According to exemplary embodiments of the present disclosure, the spring junction includes a weld region wherein the weld cap is affixed to an underlying structural member. The weld cap and the underlying structural member are advantageously configured and dimensioned to interact with the resilient element such that the resilient element is positioned in a predefined location. For example, an exemplary weld cap and structural member according to the present disclosure include opposed channels or grooves that are sized and oriented to receive the resilient element therewithin. In this way, the resilient element is properly and effectively aligned during the assembly process, and is fixed between the weld cap and the structural member upon welding of the weld cap with respect to the structural member. Indeed, according to exemplary embodiments of the present disclosure, the resilient element is captured between the weld cap and the structural member and maintained in a fixed orientation relative to the weld cap/structural member assembly due to compressive forces exerted therebetween. Additionally, one or both cooperating surfaces of the weld cap/structural member may be subjected to surface treatment(s), e.g., grip blasting, to enhance the frictional force exerted between such surface(s) and the resilient element.

Of note, the resilient element generally defines an active region intermediate a first end region and a second end region. The active region of the resilient element is generally subjected to cyclical stress, e.g., during in situ use of the disclosed spinal stabilization device. In exemplary embodiments, the weld cap is used to secure the first end region of the resilient element with respect to a first structural member, and a second weld cap is used to secure the second end region with respect to a second structural member, with the active region extending therebetween. The first and second weld caps are generally fixed with respect to the associated structural member through conventional welding processes, such as electron-beam welding. As such, the weld cap and structural member are generally subjected to welding temperatures of about 1000° F. or higher. However, the spacing of the weld region from the resilient element, which generally takes the form of a spring, e.g., a coil spring or helical spring, reduces or eliminates undesirable annealing effects on the spring.

According to further exemplary embodiments of the present disclosure, the resilient element includes first and second bend regions at either end thereof. The bend regions are sized and shaped so as to initially bend away from the helically-shaped path before bending back toward the helically-shaped path of the resilient element, e.g., the spring. The bend regions advantageously facilitate positioning of the resilient element/spring relative to the underlying structural member and weld cap. Indeed, in exemplary embodiments of the present disclosure, the structural member and the weld cap define cooperating channels or grooves that cooperate with the bend regions of the resilient element/spring for alignment and/or relatively secure positioning in advance of the welding process. Typically, a fixture is employed to fix the weld cap, resilient element and structural member during the welding process, thereby minimizing the potential for misalignment and/or reorientation during the assembly/welding processes According to further exemplary embodiments of the present disclosure, a rod is mounted with respect to (or integrally formed with) the structural member. The rod may be advantageously adapted to mount with respect to an upwardly-extending structure associated with a pedicle screw. The rod/pedicle screw may be mounted with respect to each other such that relative movement of the rod relative to the pedicle screw is permitted in at least one plane.

In a still further embodiment, a method is disclosed for producing a spring junction in which a weld cap and structural member with an end region of a resilient element positioned therebetween, and the weld cap is welded with respect to the structural member, thereby securing/capturing the end region of the resilient element therebetween. The resilient element can include a coil extending along a helically-shaped path, and in which a bend region is configured so as to initially bend away from such helical path defined before bending back toward such helical path. The bend region can extend into and/or define the end region, such that the weld cap and structural member interact with and capture, in whole or in part, the bend region of the resilient element therebetween.

In a still further embodiment, a combination is provided that includes a structural member having a first end, a second end opposite the first end, an aperture between the first end and the second end, and a notch formed in the second end. The combination also includes a resilient element having end regions at either end thereof, the end regions terminating at terminations. The resilient element is secured to the first end of the structural member such that one of the end regions is captured between a weld cap and the structural member.

The spring junction(s) of the present disclosure are typically employed as part of a spinal stabilization system that may advantageously include one or more of the following structural and/or functional attributes:

Exemplary embodiments of the spring junction (and associated spring/structural member subassembly) are capable of undergoing at least approximately 10,000,000 cycles of combined extension/contraction and bending (e.g., during mechanical testing);

Implementation of the disclosed spring junctions have no substantial effect on the footprint of the dynamic stabilization devices in which they are incorporated, e.g., the resilient elements (e.g., springs) of such spinal stabilization devices do not extend radially inwardly/outwardly or linearly to a greater extent than the dynamic stabilization devices that do not include the disclosed spring junctions, thereby preserving compatibility with existing components and/or proven or preferred geometries;

An outwardly/upwardly, then inwardly/downwardly extending bend region at each end of the resilient element, combined with channels or grooves formed in the weld cap/structural member provide an alignment which positively locates the ends of the resilient element within their respective channels/grooves during pre-welding assembly, without undue risk of annealing and/or other types of damage to the active region of the resilient element.

In addition, the noted geometric aspects of the bend region advantageously facilitate and/or enhance the mechanical integrity of the junction between the resilient element and the associated channels/grooves. Of note, a bend region having the noted geometric characteristics has reduced freedom of movement relative to the associated channels/grooves, e.g., in terms of rotation around the axis of the resilient element in the region of the junction.

Advantageous spine stabilization devices, systems and methods may incorporate one or more of the foregoing structural and/or functional attributes. Thus, it is contemplated that a system, device and/or method may utilize only one of the advantageous structures/functions set forth above, a plurality of the advantageous structures/functions described herein, or all of the foregoing structures/functions, without departing from the spirit or scope of the present disclosure. Stated differently, each of the structures and functions described herein is believed to offer benefits, e.g., clinical advantages to clinicians and/or patients, whether used alone or in combination with others of the disclosed structures/functions.

Additional advantageous features and functions associated with the devices, systems and methods of the present disclosure will be apparent to persons skilled in the art from the detailed description which follows, particularly when read in conjunction with the figures appended hereto. Such additional features and functions, including the structural and mechanistic characteristics associated therewith, are expressly encompassed within the scope of the present invention.

BRIEF DESCRIPTION OF THE DRAWINGS

To assist those of ordinary skill in the art in making and using the disclosed devices, systems and methods for achieving enhanced reliability, dependability, and/or durability, e.g., in a dynamic spinal stabilization device, reference is made to the appended figures wherein.

DESCRIPTION OF EXEMPLARY EMBODIMENTS

The present disclosure provides advantageous devices, systems and methods for improving the reliability, dependability and/or durability of spinal stabilization systems. More particularly, the present disclosure provides advantageous devices, systems and methods for mechanically mounting resilient elements (e.g., torsion springs and/or coil springs) to, and/or for coupling resilient elements between, structural members (e.g., plates, caps, flanges, rods, and/or bars) associated with dynamic spinal stabilization systems. The mounting and/or coupling methods/techniques of the present disclosure provide enhanced reliability, dependability and/or durability without significantly increasing material weight or volume requirements and without compromising the important functions of the dynamic spinal stabilization devices/systems of which they form a part.

The exemplary embodiments disclosed herein are illustrative of the advantageous spinal stabilization devices/systems and surgical implants of the present disclosure, and of methods/techniques for implementation thereof. It should be understood, however, that the disclosed embodiments are merely exemplary of the present invention, which may be embodied in various forms. Therefore, the details disclosed herein with reference to exemplary dynamic spinal stabilization systems and associated methods/techniques of assembly and use are not to be interpreted as limiting, but merely as the basis for teaching one skilled in the art how to make and use the advantageous dynamic spinal stabilization systems and alternative surgical implants of the present disclosure.

Figure 1:
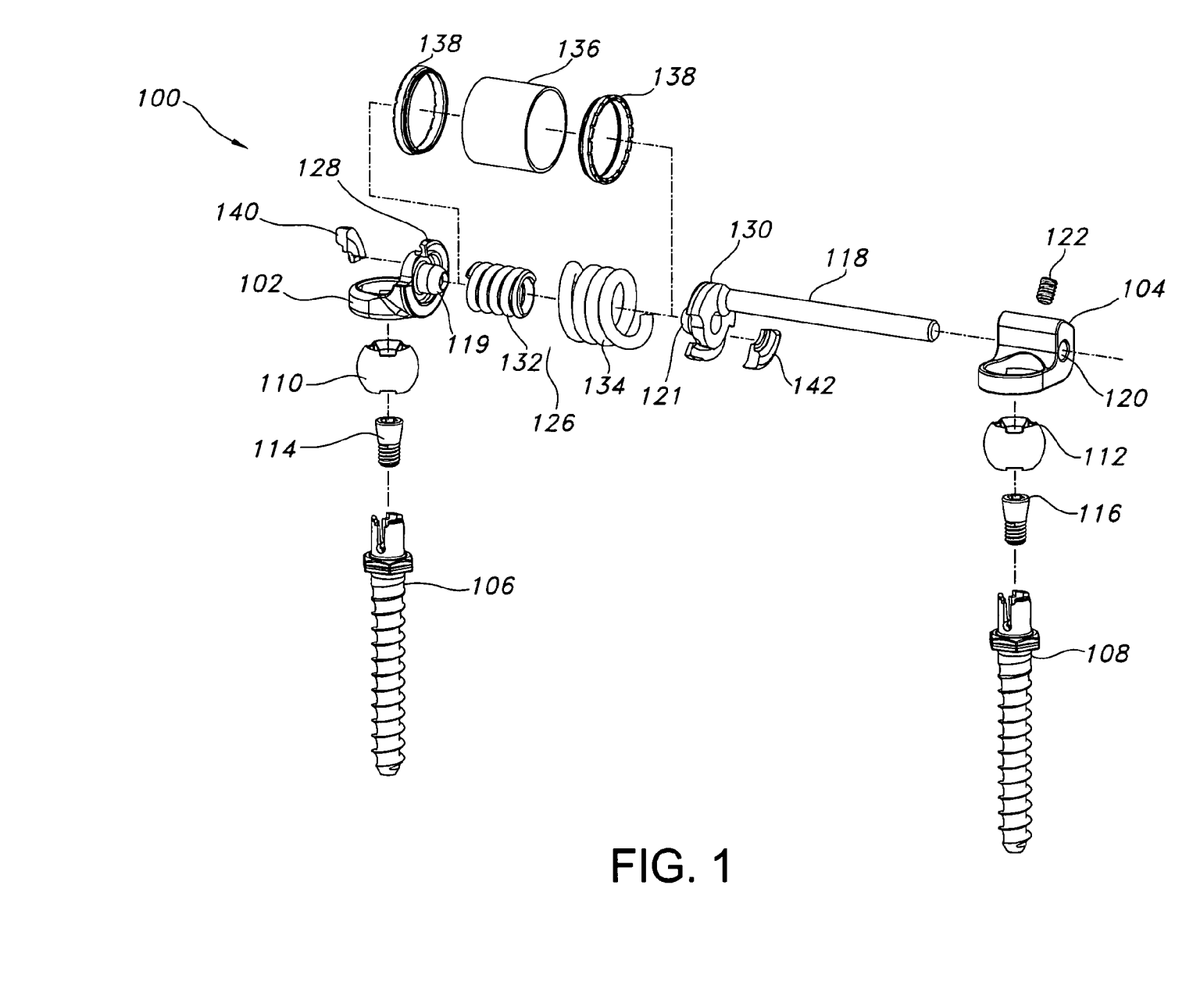
FIG. 1 is an exploded assembly view of a spinal stabilization device/system, including pedicle screws and associated mounting structures, in accordance with an exemplary embodiment of the present disclosure.
Figure 2:
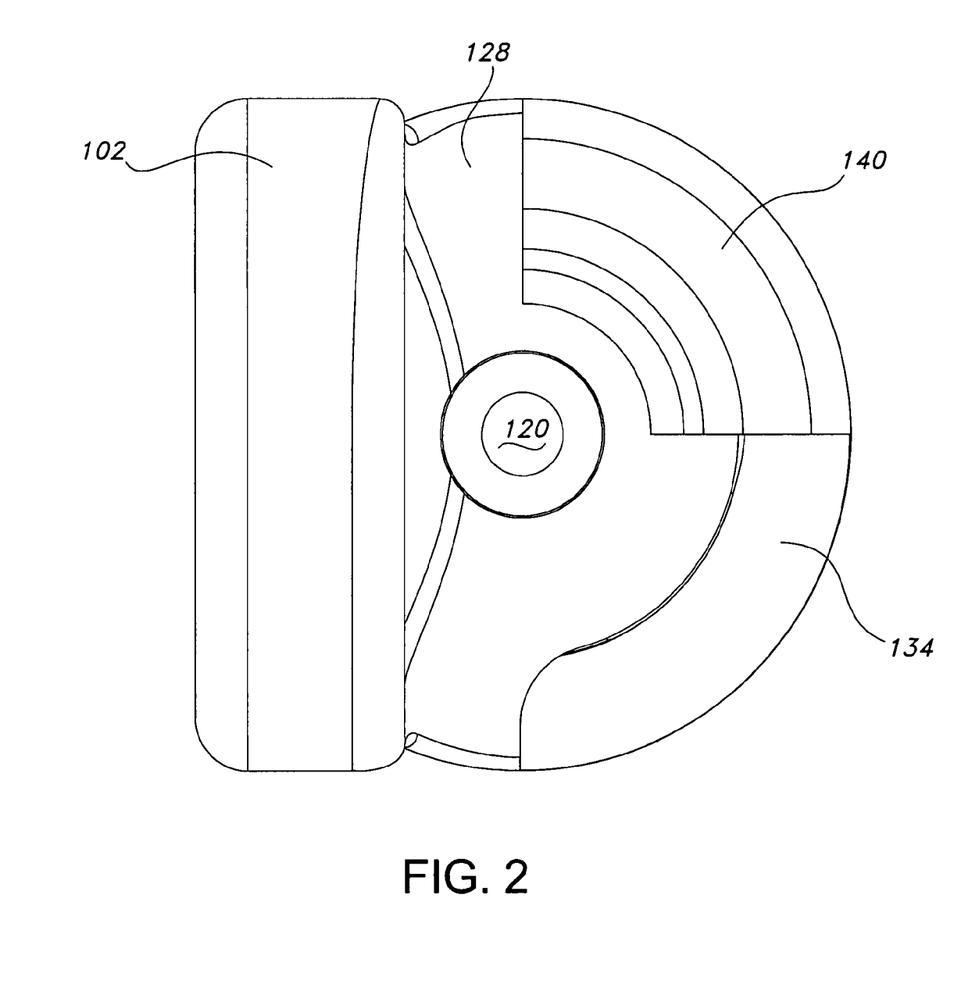
FIG. 2 is a side view (from the left side) of the spinal stabilization device schematically depicted in FIG. 1 according to an exemplary embodiment of the present disclosure.

With reference to FIG. 1, components of a dynamic stabilization element 100 disclosed in commonly assigned U.S. Non-Provisional patent application Ser. No. 11/027,270, filed Dec. 31, 2004 (hereinafter "the '270 application"), are shown in an exploded view. The disclosure of the '270 application is hereby incorporated herein by reference in its entirety. As shown in FIG. 1, the dynamic stabilization system 100 includes a dynamic stabilization device 126 that includes two structural elements in the form of a first spring cap 128 and a second spring cap 130, and two resilient elements in the form of an inner spring 132 and an outer spring 134. The first spring cap 128 is affixed to an attachment member 102 that is configured to be coupled to the head of a pedicle screw 106, preferably via a dynamic joint 110. The second spring cap 130 is affixed to a rod 118 that is configured to be attached to another attachment member 104 that is in turn coupled to the head of another pedicle screw 108, preferably via another dynamic joint 112. The dynamic stabilization system 100, and particularly the dynamic stabilization device 126, permits limited degrees of relative axial/longitudinal motion as well as angular/rotational motion.

The inner spring 132 consists of a plurality of coils sharing a common diameter and arranged sequentially about a common axis. The outer spring 134 also consists of a plurality of coils sharing a common diameter and arranged sequentially about a common axis. In the assembled state, the inner spring 132 is positioned within the outer spring 134. The coil at the end of the inner spring 132 is positioned on or around post 119 that extends from spring cap 128, and against the interior end of spring cap 128 so as to occupy (at least in part) an annular channel formed therein. A coil at the opposite end of the inner spring 132 is positioned on or around post 121 of the spring cap 130 and against the interior end of the spring cap 130 so as to occupy (at least in part) an annular channel formed therein. In this way, the inner spring 132 is effectively captured between the first spring cap 128 and the second spring cap 130 and effectively floats relative to the opposing posts 119, 121.

Figure 3:
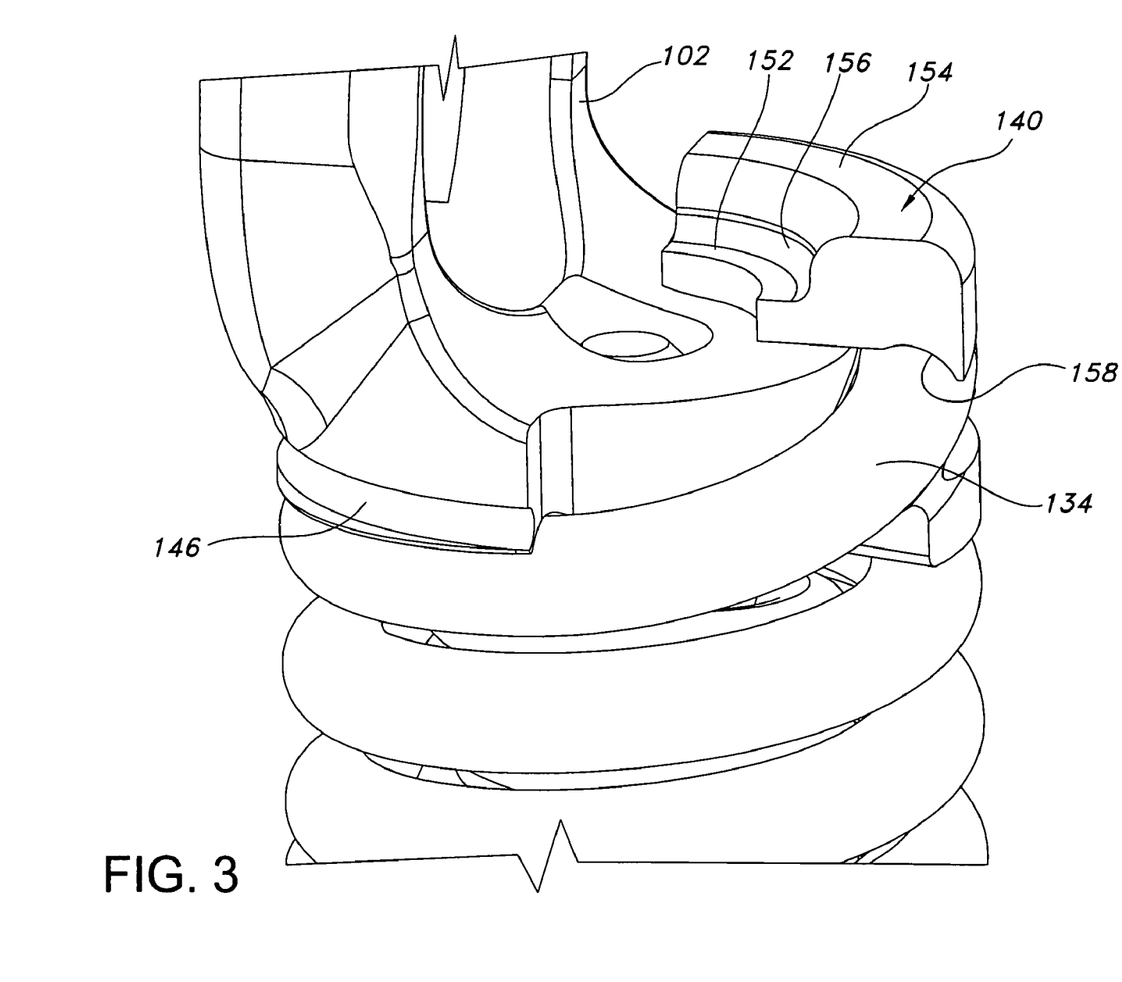
FIG. 3 is a side view of a portion of the spinal stabilization device of FIGS. 1 and 2 showing interaction between an exemplary weld cap and associated structural members.
Figure 4:
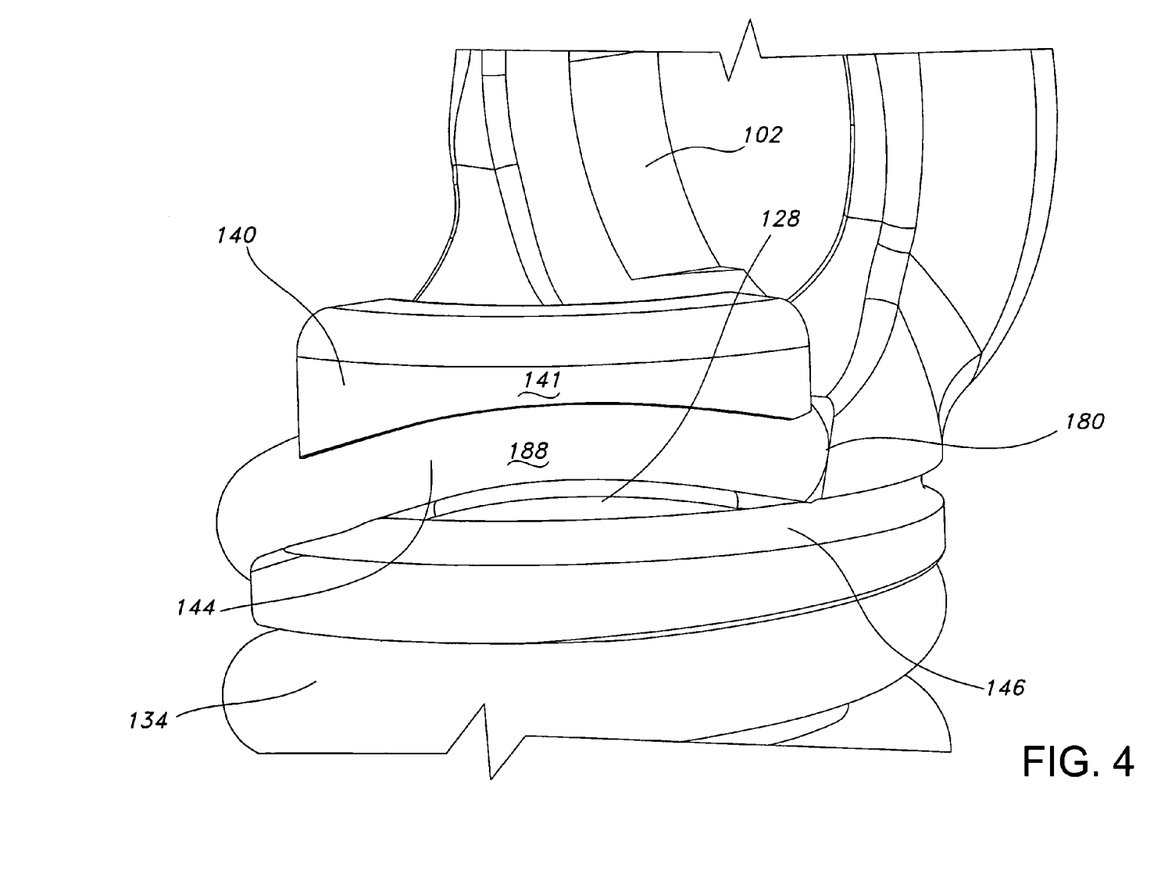
FIG. 4 is a further side view of a portion of the exemplary spinal stabilization device schematically depicted in the foregoing figures.

The spinal stabilization device 126 further includes a sheath member 136 and two end clamps 138. When assembled, the inner resilient element 132 and outer resilient element 134 are positioned within the sheath member 136, and an end clamp 138 secures the sheath member 136 to each of the structural members 128, 130. This prevents undesirable interaction or interference between the inner and outer resilient elements 132, 134 and anatomical structures in situ. As shown in FIGS. 3 and 4, a peripheral groove 146 may be formed in the structural member, e.g., end cap 128, to facilitate positioning of end clamp 138. Once positioned in or adjacent peripheral groove 146, end clamp 138 is advantageously crimped or swaged into engagement with end cap 128.

Figure 5:
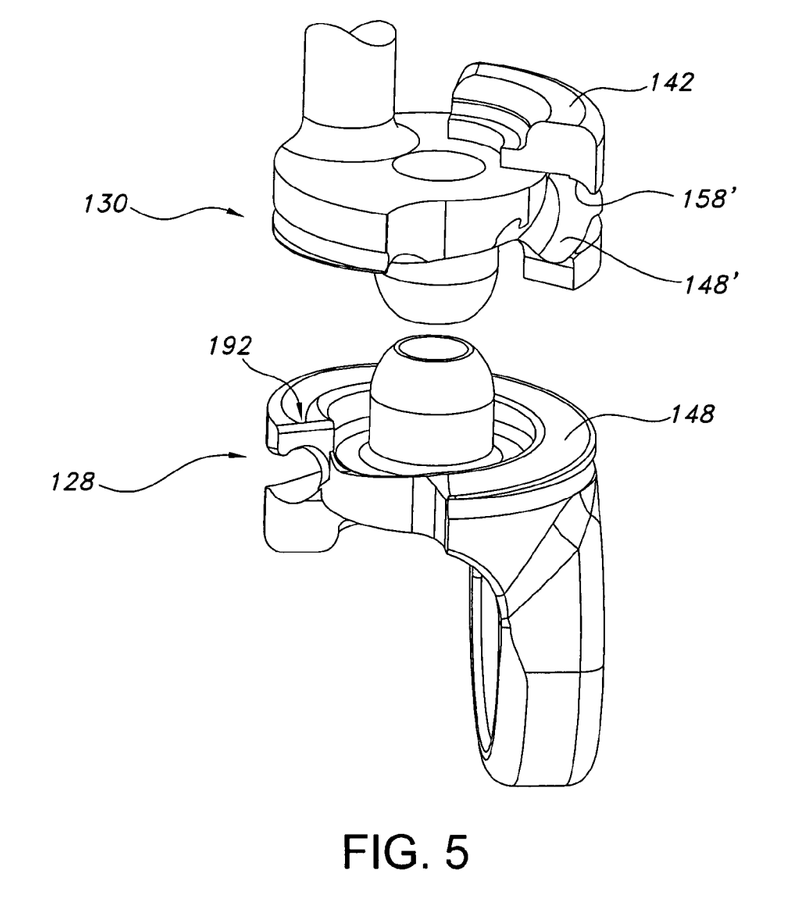
FIG. 5 is a side view of an exemplary spinal stabilization device, with parts removed for clarity.
Figure 6:
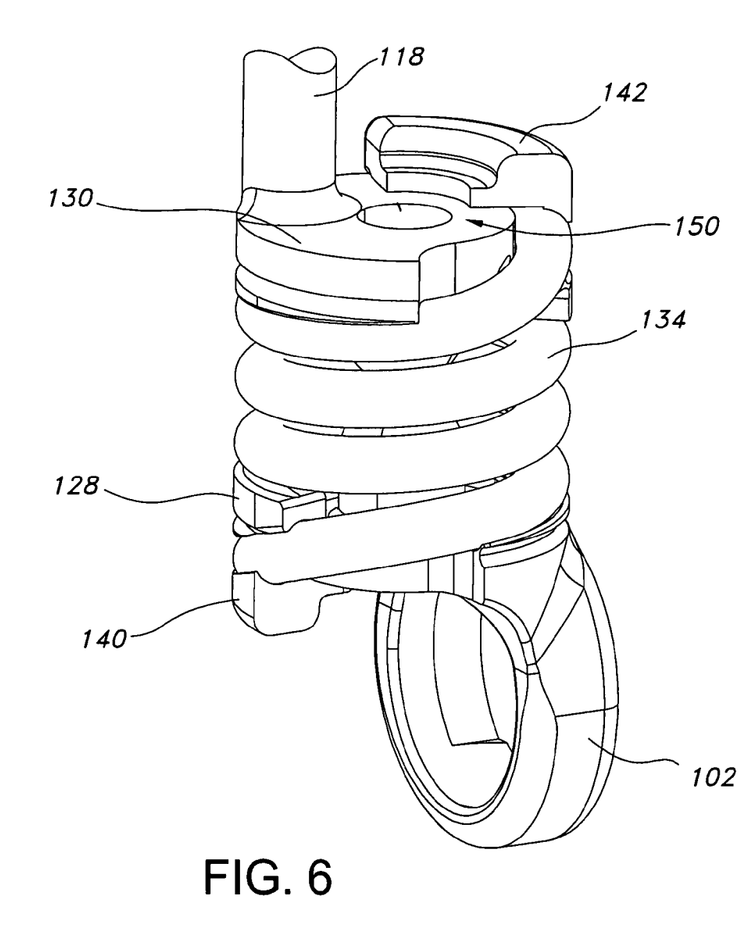
FIG. 6 is a perspective view of an exemplary spinal stabilization device that schematically depicts welding of a weld cap with respect to an underlying structural member according to the present disclosure.

With reference to FIGS. 1-8, weld caps 140 and 142 function to secure outer resilient element/spring 134 relative to structural members/end caps 128 and 130, respectively. With particular reference to FIGS. 2-4 and 6, weld cap 140 and end cap 128 cooperate to capture the end region 144 of outer spring 134 therebetween, thereby positively securing outer spring 134 with respect to end cap 128. As best seen in FIG. 4, the coil at the end of the outer spring 134 is threaded into spring cap 128. With reference to FIG. 5, helically-shaped grooves 148, 148' are defined in end caps 128, 130, respectively. The dimensional parameters associated with grooves 148, 148' are advantageously selected to cooperate with the diameter of the spring wire defining outer spring 134. FIG. 6 schematically depicts welding material 150 interacting with weld cap 142 so as to secure/capture outer spring 134 relative to end cap 130.

As described in the '270 application, the outer spring 134 is typically shorter than the inner spring 132, such that as the first spring cap 128 and the second spring cap 130 are brought toward each other (i.e., to permit the outer spring 134 to be mounted on both), the inner spring 132 is placed in compression. The degree to which the inner spring 132 is compressed is generally dependent on the difference in length as between the inner and outer springs 132, 134. Thus, the preload compression of the inner spring 132 may be controlled and/or adjusted in part through selection of the relative lengths of the inner and outer springs 132, 134. In addition to the preload compression of the inner spring 132, the mounting of the outer spring 134 with respect to the spring caps 128, 130 generally includes placing the outer spring 134 in tension. The overall preload of the dynamic stabilization device 126 corresponds to equal and opposite forces experienced by and/or contained within the inner and outer springs 132, 134.

The inner spring 132 reaches its free length (i.e., non compressed state) at or about the point at which a patient's movement exceeds a "neutral zone" (as described more completely in the '270 application). Beyond this point, the inner spring 132 is free floating (e.g., on the opposing posts 119, 121), while the outer spring 134, already in tension, extends in length even further.

In the overall design of the disclosed spinal stabilization system, optimization of the attachment between the outer spring 134 and spring caps 128, 130 is desirable. In experimental studies associated with spinal stabilization devices of the type disclosed herein, it has been noted that direct welding of the outer spring 134 and spring caps 128, 130 may not provide an optimal means of attachment. While not intending to be bound by theory, it is believed that a "heat-affected" zone may be created in the coil at the end region 144 of the outer spring 134 as a result of the process of welding the outer spring 134 to the spring caps 128, 130. More particularly, such heat-affected zone is believed to arise as a result of an annealing effect brought about by the migration of excess heat arising from an electronic-beam welding process. In accordance with such electronic beam or E-beam welding processes, elevated temperatures in a range of approximately 1000° F. or higher are used to affix the outer spring 134 to the spring cap 128, 130 by essentially melting such components together. The heat-affected zone so produced can be at least 0.005"-0.030" in axial length, and is located immediately adjacent the weld formed at the end of the outer spring 134, and along the active region of the outer spring 134. (As used herein in reference to a spring or resilient element, the term "active region" or "active portion" refers to a region, portion, or part of the spring or resilient element which, during normal in-situ use and/or representative mechanical testing of the spring or resilient element, actively contributes to the characteristic stiffness of the spring or resilient element, and/or actively participates in the axial travel and/or lateral bending thereof.) The heat-affected zone can include a soft or weak point on the coil at which a Rockwell hardness of the material of the outer spring 134, ordinarily falling within a range of from approximately 46 to approximately 54, dips sharply; e.g., to a value in a range of from approximately 20 to approximately 24.

According to the present disclosure, geometric/structural modifications to the outer spring 134 and the spring caps 128, 130, together with incorporation of weld caps 140, 142 into the overall assembly, have been found to advantageously enhance the reliability and durability of dynamic stabilization device 126. Exemplary embodiments of the advantageous geometric/structural modifications to the outer spring 134 and spring caps 128, 130, as well as the incorporation of weld caps 140, 142, are described hereinbelow with reference to FIGS. 2-7. As a result of these geometric/structural modifications and the incorporation of weld caps 140, 142, a durability standard of 10,000,000+ failure-free cycles is believed to be achievable on a sustained and reliable basis.

According to exemplary embodiments of the present disclosure, the geometric/structural modifications include the creation of a substantial physical separation of the active portion of the outer spring from the heat-affected zone associated with the E-beam welding process, and/or from the actual site of the weld formed between the attached components. As a result of this separation, to the extent that any region of the outer spring becomes significantly annealed, and/or is brought to a significantly lowered Rockwell hardness value as a result of E-beam welding, the amount of cyclic stress to which that softened or annealed portion is exposed is substantially reduced and/or brought to such a low level that the respective junctions between the outer spring and its associated spring caps can exhibit very high levels of reliability/durability.

Thus, with further reference to FIG. 1 and as previously described in part above, dynamic spinal stabilization system 100 is shown in accordance with an exemplary embodiment of the present disclosure. The exemplary dynamic stabilization system 100 includes attachment members 102, 104, pedicle screws 106, 108, ball/spherical elements 110, 112, and set screws 114, 116. The attachment member 102 is configured to receive the ball/spherical element 110. The ball/spherical element 110 then receives the head of the pedicle screw 106 such that a global/dynamic joint is formed between the attachment member 102 and the head of the pedicle screw 106. The set screw 114 is then inserted into the head of the pedicle screw 106, thereby securing the head of the pedicle screw 106 within the ball/spherical element 110. The attachment member 104 is configured to receive the ball/spherical element 112. The ball/spherical element 112 then receives the head of the pedicle screw 108 such that a global/dynamic joint is formed between the attachment member 104 and the head of the pedicle screw 108. The set screw 116 is then inserted into the head of the pedicle screw 108, thereby securing the head of the pedicle screw 108 within the ball/spherical element 112.

As noted previously, the spinal stabilization system 100 also includes rod 118. The rod is configured to be inserted into the attachment member 104, which includes a transverse aperture 120 to accommodate the rod 118, and a set screw 122 to secure the rod 118 at a desired position within the transverse aperture 120, e.g., employing a hex driver (not shown).

Dynamic stabilization element 126 includes structural members 128, 130, an inner resilient element 132, an outer resilient element 134, a sheath member 136, and two end clamps 138. In the disclosed exemplary embodiment, the structural member 128 is affixed to (e.g., is of unitary construction with) the attachment member 102 and takes the form of a plate having multiple features permitting the structural member 128 to function in the manner of an end cap or spring cap with respect to the inner and outer resilient elements 132, 134. Similarly, the structural member 130 is affixed to (e.g., is of unitary construction with) the rod 118 (which is positioned off-axis or off-center with respect to the structural member 130), and takes the form of a plate having multiple features permitting the structural member 130 to function in the manner of an end cap or spring cap with respect to the inner and outer resilient elements 132, 134.

Referring now to FIG. 4, the outer resilient element 134 consists of a plurality of coils sharing a common diameter and arranged sequentially about a common axis between a coil termination 180 at an end of the outer resilient element 134 and a coil termination (not shown) at an opposite end thereof. Extending from the coil termination 180, and substantially continuous therewith, is a bend region 188 of the outer resilient element 134. According to exemplary embodiments of the present disclosure, a corresponding coil termination and bend region are defined at the opposite end of the outer resilient element 134. As shown in FIG. 4, weld cap 140 advantageously includes a substantially arcuate geometry 141 to track the bend region 188 of spring 134.

In exemplary embodiments of the present disclosure, the bend regions, e.g., bend region 188, of the outer resilient element/spring 134 extend peripherally from the respective coil terminations, e.g., coil termination 180, along respective paths which, when viewed axially from either end of the outer resilient element/spring 134, are defined by respective single radii that extend from the common axis of the coils of the outer resilient element 134 and that have extents approximately half that of the common diameter of the coils. As a result, the bend regions, e.g., bend region 188, of the outer resilient element/spring 134 remain within the same peripheral outline defined by the coils of the outer resilient element 134. When viewed from the side, however, as in FIG. 4, bend region 188 of the outer resilient element 134 is seen to depart from the helical path defined by the coils.

More particularly, the bend region 188, when viewed from the side as in FIG. 4, is seen to include a curve or bend in the path of extension of the bend region 188, according to which the material of the outer resilient element/spring 134: (1) initially curves away from the adjacent coil at the coil termination 180; (2) reaches an apex representing a point of maximum departure from the adjacent coil; and (3) curves therefrom back toward the adjacent coil to return to the helical path defined by the coils.

In the assembled state of the dynamic stabilization device 126, the inner resilient element 132 is positioned within the outer resilient element 134, between the respective posts 119, 121, and within the respective annular channels of the structural elements 128, 130. The bend region 188 and the coil at the end of the outer resilient element 134 are threaded into the interior end of the structural element 130 until the bend region 188 has substantially passed into or through an aperture formed in the structural element 130 (see, e.g., aperture 192 defined in structural member 128, as shown in FIG. 5) and the bend region termination has been caused to drop or snap into place within a notch formed in the exterior end of the structural element 130.

With particular reference to FIGS. 3 and 6, it is noted that exemplary weld caps 140, 142 according to the present disclosure define a geometry that includes a variable height/thickness. More particularly, a reduced height/thickness region 152 is defined radially inward of a greater height/thickness region 154. An arcuate transition region 156 is generally provided to transition between regions 152 and 154. The reduced height/thickness region 152 advantageously provides an effective geometry for welding of the weld caps 140, 142 relative to the underlying structural members, i.e., end caps 128, 130. Thus, as schematically depicted in FIG. 6, the weld material 150 typically interacts with the weld cap in the reduced height/thickness region 152, defining a generally sloped and/or arcuate geometry relative to the axis of the spinal stabilization device 126. The greater height/thickness region 154 in turn provides sufficient material to ensure effective compression/capture of outer spring 134. As shown in FIGS. 3 and 5, helical channels 158, 158' are defined in the undersurface of region 154 of weld caps 140, 142 to facilitate alignment and capture of the end region (e.g., end region 188) of outer spring 134.

Weld caps 140, 142 are generally fabricated from an appropriate metal, e.g., cobalt chrome, titanium, stainless steel or the like. The circumferential/angular extent of weld caps 140, 142 is generally selected to ensure sufficient clamping/compressive force is exerted on outer spring 134, e.g., to ensure that the end region of the outer spring is without freedom of movement in any axis, e.g., axial, rotational or a combination thereof. Indeed, to enhance the clamping/compressive force exerted on outer spring 134, surface treatment(s) may be undertaken to increase/enhance the gripping forces associated with the weld cap and/or opposed grove/channel surfaces associated with the corresponding end cap. Thus, for example and with reference to FIG. 5, surfaces 148' and 158' may be advantageously grip blasted to increase the frictional forces imparted thereby when clamped/compressed into engagement with a resilient member, e.g., spring 134. Alternative surface treatment modalities may also be employed, e.g., sand blasting, abrasive blasting, surface etching and the like, as will be apparent to persons skilled in the art.

In exemplary embodiments of the present disclosure, weld caps 140, 142 each define a circumferential/angular extent of about 90° to about 160°, although geometries outside the noted range are contemplated based on the overall design of the spinal stabilization device/system and the forces to be encountered thereby. Exemplary heights in region 154 are between about 0.45 inches and 0.55 inches, while exemplary heights in region 152 are between 30% and 60% of the height of region 154. Of note, the geometry of weld caps 140, 142 in region 152 may be substantially planar or non-planar, provided adequate surface geometry is provided to accommodate and effect a desired welding operation.

In the assembly process, components that define the spinal stabilization device 126, i.e., inner spring 132, outer spring 134, and end caps 128, 130, are combined to define a sub-assembly. Weld caps 140, 142 are positioned with respect to the sub-assembly such that the end regions of the outer spring 134 are aligned with the channels/grooves 158, 158' formed in the underside of the weld caps, and the sub-assembly is then generally fixtured so as to place the weld cap/end cap region in compression. Of note, in exemplary embodiments of the present disclosure, a minimal clearance may exist between the weld flange 154 and the corresponding end caps 128, 130, e.g., about 0.0005 to about 0.003 inches, prior to application of the fixturing compression. Once fixtured, a welding operation is generally initiated such that welding material 150 is applied to the weld cap/end cap interface as schematically depicted in FIG. 6, thereby securing the weld caps 140, 142 with respect to the corresponding end caps 128, 130 and locking outer spring 134 therebetween. The disclosed assembly technique advantageously maintains a distance or spacing between the welding heat effects and the outer spring 134, such that undesirable annealing effects are avoided in the active region of the outer spring 134. Thus, the disclosed system design and assembly technique provides an efficient, reliable and effective approach to ensuring product integrity while avoiding any deleterious effects on the disclosed dynamic/spring system.

Figure 7:
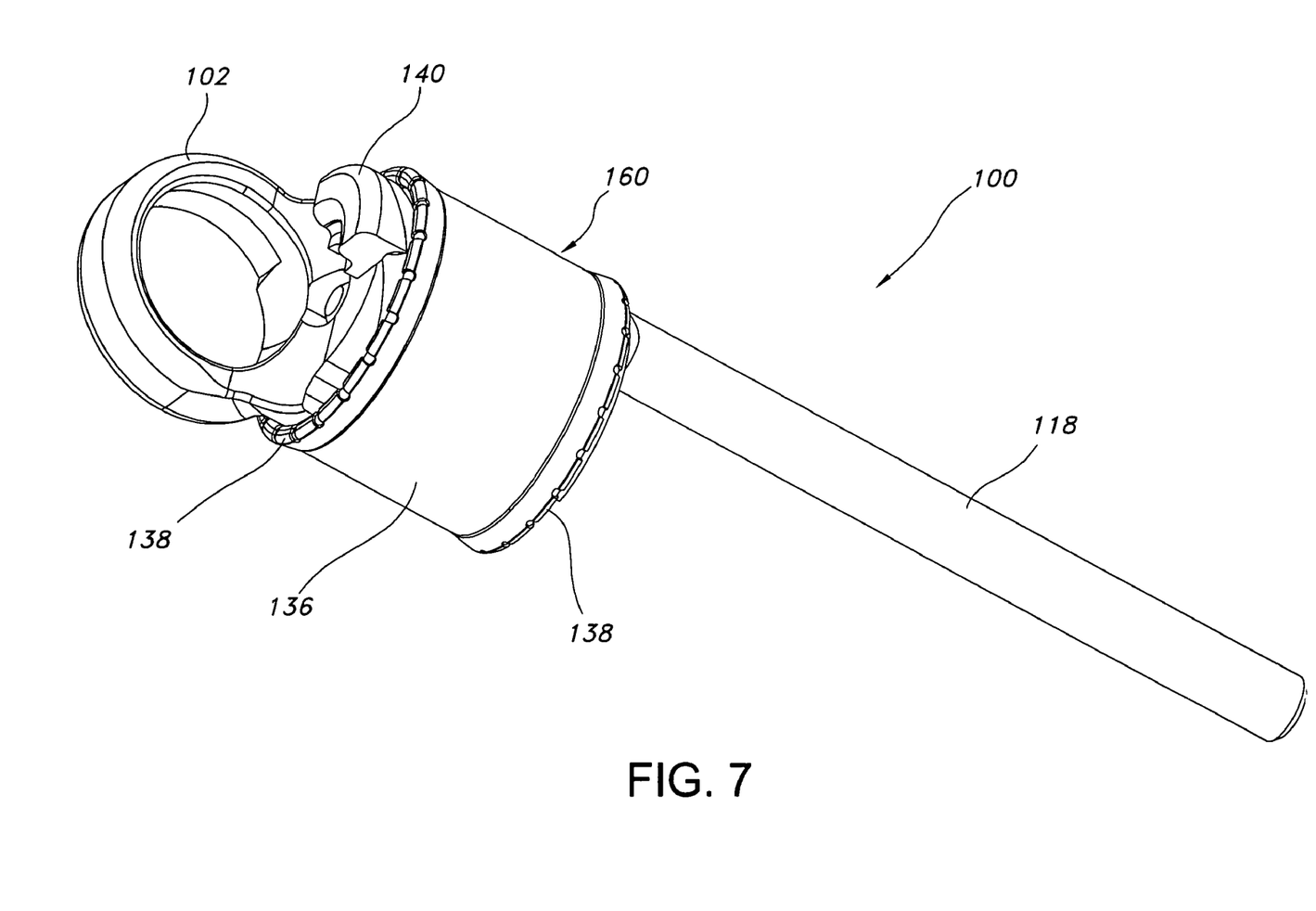
FIG. 7 is a perspective view of an assembled spinal stabilization device/system according to an exemplary embodiment of the present disclosure.
Figure 8:
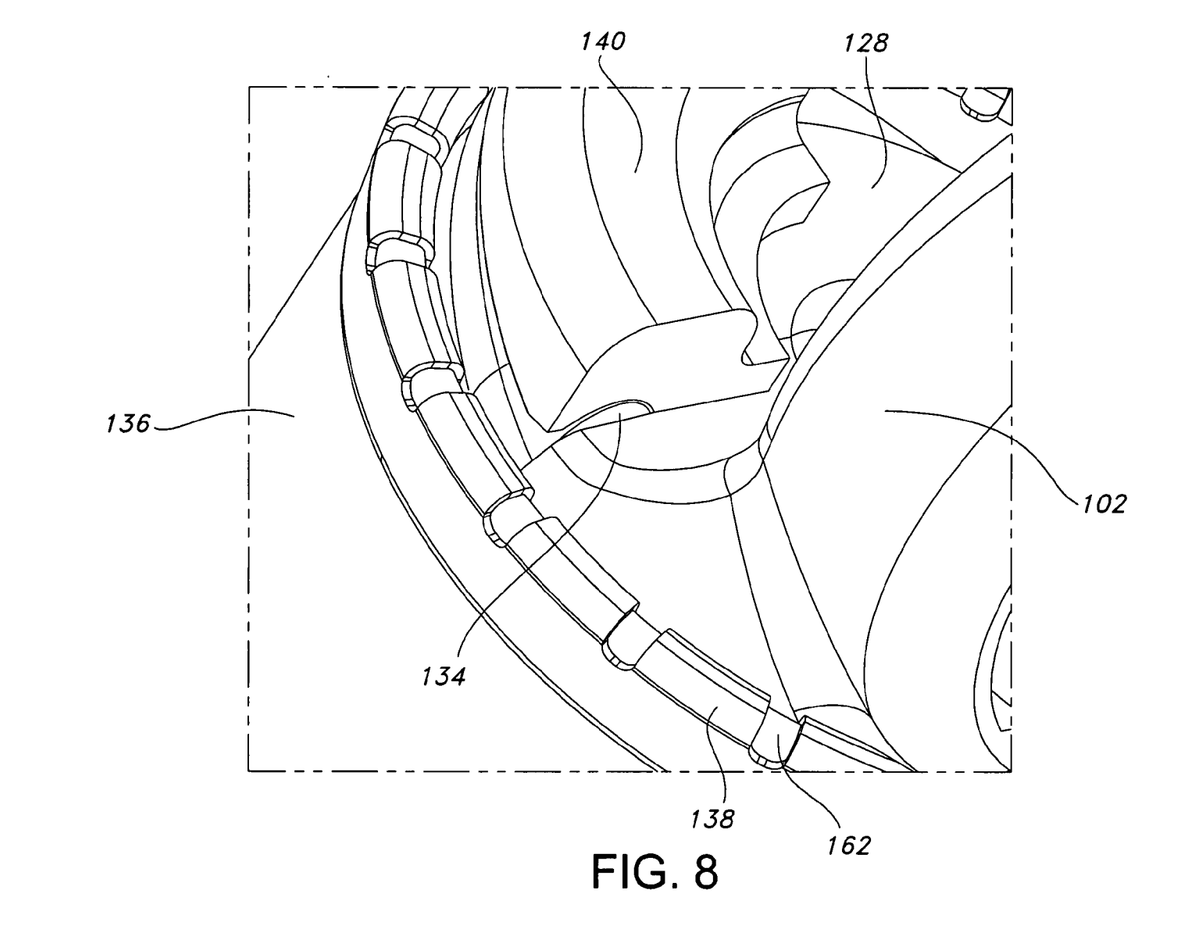
FIG. 8 is a top perspective view of a portion of the exemplary spinal stabilization device/system of FIG. 7.

With reference to FIGS. 7 and 8, exemplary embodiments of the present disclosure further contemplate incorporation of a sheath assembly 160 over or concentrically around the spring members 132, 134. Sheath assembly 160 generally includes sheath member 136 and end clamps 138. With particular reference to FIG. 8, exemplary end clamps 138 include circumferentially spaced notches 162 that facilitate interaction between the end clamps 138 and the sheath member 136, and further facilitate assembly of the sheath assembly 160 with respect to the underlying end cap 128. Of note with respect to the schematic depiction of FIG. 8, the weld material 150 has been omitted for clarity purposes.

The dynamic stabilization device 126 associated with the spinal stabilization system 100 described hereinabove provides numerous advantages. For example, improved reliability and durability may be achieved with the disclosed dynamic stabilization device based at least in part on the fact that the heat-affected zone associated with the process of securing the outer resilient element 134 with respect to the structural elements 128, 130 via welding and use of weld caps 140, 142 is physically separated from the active region of the outer resilient element 134, and is therefore isolated from the cyclical stress associated with repeated extension/contraction and/or bending during normal use and/or representative mechanical testing. In other words, to the extent the use of E-beam welding reduces the Rockwell hardness of a portion or portions of the outer resilient element 134, it is expected that, according to the present disclosure, such portion or portions will be substantially completely shielded from fatigue-producing levels of cyclic stress.

The dynamic stabilization device 126 associated with the spinal stabilization system 100 described hereinabove can be the subject of numerous modifications and variations while still exhibiting the above-discussed advantages over other dynamic junctions for spinal stabilization systems. For example, the rod 118 can be repositioned to an axial position with respect to the structural member 130. The weld caps 140, 142 can be affixed to the structural members 128, 130 by other welding processes than E-beam welding, and/or by one or more non-welding means of attachment, such as by clamping or the use of mechanical fasteners appropriate for use in conjunction with small gage springs, by an adhesive-based process, or via the use of a single mold to form the two components together as a single piece. To the extent such attachment schemes result in respective attachment regions, such attachment regions are similarly disposed physically separately relative to the respective active region of the outer resilient element 134 (whether or not heat-affected zones are present), and are thereby similarly shielded from the types and levels of cyclical stress known to produce fatigue failure. The outer resilient element 134 need not necessarily be configured in the manner of a coil spring, but may instead take the form of one or more other types of resilient elements, such as a leaf spring, a torsion spring or bar, etc. Additionally, the outer resilient element 134 may be employed in a dynamic junction that does not also include the inner resilient element 132. Many other variations and/or modifications are possible.

Although the present disclosure has been disclosed with reference to exemplary embodiments and implementations thereof, those skilled in the art will appreciate that the present disclosure is susceptible to various modifications, refinements and/or implementations without departing from the spirit or scope of the present invention. In fact, it is contemplated the disclosed connection structure may be employed in a variety of environments and clinical settings without departing from the spirit or scope of the present invention. Accordingly, while exemplary embodiments of the present disclosure have been shown and described, it will be understood that there is no intent to limit the invention by such disclosure, but rather, the present invention is intended to cover and encompass all modifications and alternate constructions falling within the spirit and scope hereof.

The invention claimed is:

1. A spinal stabilization device comprising:
   a. at least one spring member defining a helical geometry and an end region;
   b. a structural member defining a threading channel for interaction with the at least one spring member, wherein the threading channel defines an aperture that is in helical alignment with a helically-shaped groove defined on an outer face of the structural member; and
   c. a weld cap defining a helical channel groove on an in inner face for cooperation with the helically-shaped groove on the outer face of the structural member to capture the end region of the at least one spring member between the helical groove defined on the inner face of the weld cap and the helically-shaped groove defined on the outer face of the structural member;
   wherein the at least one helical spring member is threaded within the threading channel of the structural member such that the end region passes through the aperture defined by the threading channel and rests in the helically-shaped groove on the outer face of the structural member; and
   wherein the weld cap is welded with respect to the structural member with the end region of the at least one helical spring positioned therebetween, thereby securing the end region of the at least one spring member between the weld cap and the structural member.

2. A spinal stabilization device according to claim 1, wherein the structural member is an end cap.

3. A spinal stabilization device according to claim 1, wherein the at least one spring member further defines a bend region in the end region that functions to maintain alignment of the at least one spring member relative to the structural member prior to the welding of the weld cap with respect to the structural member.

4. A spinal stabilization device according to claim 1, wherein the bend region is effective to reduce freedom of movement of the at least one spring member relative to the structural member.

5. A spinal stabilization device according to claim 1, wherein the helically-shaped groove on the outer face of the structural member defines a surface, and wherein the surface includes a surface treatment.

6. A spinal stabilization device according to claim 5, wherein the surface treatment is effective to increase frictional forces imparted to the at least one spring member.

7. A spinal stabilization device according to claim 5, wherein the surface treatment is effected by grip blasting.

8. A spinal stabilization device according to claim 1, wherein the weld cap includes a greater height region and a radially inward region of lesser height.

9. A spinal stabilization device according to claim 8, wherein an arcuate or angled transition region is defined between the greater height region and the lesser height region.

10. A spinal stabilization device according to claim 1, wherein the weld cap is fabricated from a metal selected from the group consisting of cobalt chrome, titanium and stainless steel.

11. A spinal stabilization device according to claim 1, wherein the weld cap defines an angular extent of between about 90° and 160°.

12. A spinal stabilization device according to claim 1, further comprising a second spring member positioned concentrically internal to said at least one spring member.

13. A spinal stabilization device according to claim 1, further comprising a sheath assembly positioned around said at least one spring member.

14. A spinal stabilization device according to claim 1, further comprising a second structural member spaced from said structural member, and a second weld cap configured and dimensioned for capturing an opposite end of said at least one spring member between the second weld cap and the second structural member.

15. A spinal stabilization device according to claim 1, wherein welding of the weld cap with respect to the structural member does not affect spring properties of an active region of the at least one spring member.

16. A spinal stabilization system, comprising:
   a. a spinal stabilization device including
      i. at least one spring member defining a helical geometry, at least one bend region that diverges from said helical geometry at each end thereof, and an end region at each end thereof;
      ii. a pair of structural members, each of said pair of structural members defining a threading channel for threading interaction with the at least one spring member, wherein the threading channel defines an aperture at each end thereof in helical alignment with a helically-shaped groove defined on an outer face of each structural member; and
      iii. a pair of weld caps, each of the weld caps defining a helical channel groove on an in inner face for cooperation with the helically-shaped groove on the outer face of the structural member to capture the corresponding end region of the at least one spring member between the helical groove defined on the inner face of the weld cap and the helically-shaped groove defined on the outer face of the structural member; wherein the at least one bend region is adapted to interact with the outer face of the structural member, and wherein the at least one helical spring member is threaded within the respective threading channels of the structural members such that the end region passes through the corresponding aperture defined by the threading channel and rests in the helically-shaped groove on the outer face of the structural member; and wherein each weld cap is welded with respect to a corresponding structural member with the end region of the at least one helical spring positioned therebetween, thereby securing each end region of the at least one spring member between the weld cap and an associated structural member; and b. a pedicle screw mounted with respect to each of the structural members.

* * * * *